(12) United States Patent
Usuda et al.

(10) Patent No.: US 9,017,368 B2
(45) Date of Patent: Apr. 28, 2015

(54) BLOOD PRESSURE CALCULATION METHOD FOR NON-INVASIVE BLOOD PRESSURE MEASUREMENT APPARATUS

(75) Inventors: Takashi Usuda, Tokyo (JP); Sunao Takeda, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 802 days.

(21) Appl. No.: 12/263,381

(22) Filed: Oct. 31, 2008

(65) Prior Publication Data

US 2009/0112104 A1   Apr. 30, 2009

(30) Foreign Application Priority Data

Oct. 31, 2007   (JP) ................................ 2007-283374

(51) Int. Cl.
*A61B 5/02* (2006.01)
*A61B 5/021* (2006.01)
*A61B 5/022* (2006.01)
*A61B 5/00* (2006.01)

(52) U.S. Cl.
CPC .............. *A61B 5/022* (2013.01); *A61B 5/02116* (2013.01); *A61B 5/02225* (2013.01); *A61B 5/7257* (2013.01)

(58) Field of Classification Search
USPC .......... 606/202; 600/481, 485, 490, 492, 493, 600/494, 495, 496, 501, 502
See application file for complete search history.

(56) References Cited

U.S. PATENT DOCUMENTS

| | | | |
|---|---|---|---|
| 4,313,445 A | 2/1982 | Georgi | |
| 4,360,029 A | 11/1982 | Ramsey, III | |
| 4,889,133 A * | 12/1989 | Nelson et al. | 600/494 |

FOREIGN PATENT DOCUMENTS

| | | |
|---|---|---|
| EP | 1 757 225 A | 2/2007 |
| JP | 62-157505 U | 10/1987 |
| JP | 4-259448 A | 9/1992 |
| JP | 4-285530 A | 10/1992 |
| JP | 5-184547 A | 7/1993 |
| JP | 11-56827 A | 3/1999 |
| JP | 2001-95766 A | 4/2001 |
| JP | 2002-224059 A | 8/2002 |
| JP | 2002-224061 A | 8/2002 |
| WO | 91/01682 A | 2/1991 |

OTHER PUBLICATIONS

Japanese Office Action for related Japanese Patent Application No. 2007-283374 dated Dec. 22, 2011.
Japanese Office Action for the related Japanese Patent Application No. 2007-283374 dated Jul. 26, 2012.
Japanese Office Action for the related Japanese Patent Application No. 2007-283374 dated Jan. 21, 2013.

* cited by examiner

*Primary Examiner* — Stacy B Chen
(74) *Attorney, Agent, or Firm* — Kenealy Vaidya LLP

(57) ABSTRACT

A method of calculating a blood pressure, includes: providing a non-invasive blood pressure measurement apparatus which includes a cuff being inflatable and deflatable and adapted to be fitted on a part of a living body and in which a plurality of calculation methods each of which has priority in accordance with a type of noise information are set; detecting, by the cuff, a signal waveform representing a change in an oscillation amplitude and a change in a cuff pressure; determining the type of the noise information contained in the detected signal waveform; deciding the blood pressure from at least one candidate value for the blood pressure, which is calculated by one of the calculation methods that has the priority with respect to the determined type of the noise information; and displaying the decided blood pressure.

10 Claims, 5 Drawing Sheets

| FLAG \ CALCULATION MEANS | NORMAL CALCULATION | MOVING AVERAGE | WAVELET | FILTER BANK | FFT |
|---|---|---|---|---|---|
| SINGLE NOISE | ○ | × | × | × | × |
| OSCILLATORY NOISE | × | × | ○ | ○ | ○ |
| LOW-FREQUENCY NOISE | ○ | × | × | × | ○ |
| ARRHYTHMIA | ○ | ○ | ○ | ○ | × |
| NONE | ○ | × | × | × | × |

BLOOD PRESSURE CALCULATION METHOD FOR NON-INVASIVE BLOOD PRESSURE MEASUREMENT APPARATUS

BACKGROUND OF THE INVENTION

The present invention relates to a blood pressure calculation method for a non-invasive blood pressure measurement apparatus that measures a blood pressure by means of an oscillometric method. More particularly, the present invention relates to a blood pressure for a non-invasive blood pressure measurement apparatus configured such that a cuff being inflatable and deflatable and being fitted on a part of a subject's living body detects a change in an oscillation amplitude generated from arterial pulsation and a change in a cuff pressure, that a plurality of calculation methods is prepared as a calculation method for calculating a blood pressure value, for example, when a noise is generated due to body motion of the subject or when arrythmia due to disorder is observed or an abnormal pulse wave is generated with IABP (intra-aortic balloon pumping), and that a type of the noise or the arrythmia contained in the detection signal is determined and the optimum blood pressure calculation method is selected for each of the determined types of the noise or the arrythmia, thereby calculating and displaying the optimum blood pressure value.

In the past, in a non-invasive blood pressure measurement apparatus that measures a blood pressure by means of an oscillometric method, since a pressure noise resulting from subject's body motion is greatly superposed on the pulse wave of a cuff pressure, a predetermined logic element monitors the pulse wave of the cuff pressure to determine the presence of the noise resulting from the body motion. The non-invasive blood pressure measurement apparatus is provided with a means for generating a measurement error when it is determined that the noise is present, a means for adding information that represents occurrence of the noise during measurement, a means for reducing the noise resulting from the body motion, and the like.

In the related art, an electronic manometer is proposed that can measure a blood pressure with high precision even when a subject is walking, exercising or involved in other activities (see JP-A-2002-224059). The electronic manometer disclosed in JP-A-2002-224 059 includes: (1) a means for per forming frequency analysis on a pulse wave and a noise and transforming time series data into frequency data; (2) a means for comparing the frequency data of the pulse wave with the frequency data of the noise to calculate the frequency of the pulse wave; (3) a means for eliminating frequency components other than the frequency component of the pulse wave from the frequency data of the pulse wave; and (4) a means for transforming the frequency data of the pulse wave having other frequency components of the pulse wave eliminated therefrom into time series data to restore the pulse wave. Then, the electronic manometer calculates a blood pressure based on the restored pulse wave.

According to the electronic manometer disclosed in JP-A-2002-224059 having such a configuration, as a means for detecting a noise resulting from subject's body motion, a velocity sensor, an acceleration sensor, a position sensor, a displacement sensor, an angle sensor, a direction sensor, and an inclination sensor are used. In this case, when a photoelectronic sensor, for example, detects a photoplethysmograph signal and a noise resulting from subject's body motion is not present in the pulse wave signal, only a frequency component of the photoplethysmograph is present in the power spectrum of the photoplethysmograph, and no characteristic spectrum is present in the power spectrum of an acceleration signal. However, when the noise resulting from subject's body motion is present in the pulse wave signal, both a frequency component of the photoplethysmograph and a frequency component of the body motion are present in the power spectrum of the photoplethysmograph, and a spectrum of the frequency component of the body motion is present in the power spectrum of the acceleration signal. Therefore, the frequency component of the photoplethysmograph can be extracted by comparing the power spectrum of the photoplethysmograph with the power spectrum of the acceleration signal. That is, it is possible to remove the noise resulting from the body motion or the like from a pulse wave and calculate an appropriate blood pressure value based on the pulse wave.

Moreover, as a method for eliminating a noise resulting from subject's body motion or the like, contained in a pulse wave propagation signal detected from the subject, there are known (1) a method that compares a amplitude value (amplitude value) or an interval of pulse waves before and after a pulse wave signal of a cuff pressure and eliminates a waveform determined as being a noise; (2) a method that calculates moving average values of a plurality of varying amplitudes of a pulse wave signal of a cuff pressure; and (3) a method that eliminates a noise from a pulse wave signal of a cuff pressure by means of a mathematical method such as filter bank, FFT, or wavelet (see JP-A-2002-224061 and JP-A-2001-095766).

However, in the related-art blood pressure measurement method or blood pressure calculation method, when detecting the noise resulting from the body motion or the like to measure or calculate the blood pressure value, elimination of the noise or the determination as to invalidate or eliminate the measurement or calculation is performed by using one of the method described above. Therefore, the related-art method may not be the optimum calculation method depending on patients in various states and conditions, and it is thus difficult to perform the blood pressure measurement or calculation in a quick and appropriate manner.

SUMMARY

It is therefore an object of the invention to provide a blood pressure calculation method for use in a non-invasive blood pressure measurement apparatus capable of determining a type of a noise due to subject's body motion or arrythmia due to disorder from a change in a cuff pressure or a change in an oscillation amplitude detected or measured from a subject and appropriately selecting a corresponding blood pressure calculation method based on the determination result, thereby calculating and displaying the optimum blood pressure value in a quick and appropriate manner.

In order to achieve the object, according to the invention, there is provided a method of calculating a blood pressure, comprising:

providing a non-invasive blood pressure measurement apparatus which includes a cuff being inflatable and deflatable and adapted to be fitted on a part of a living body and in which a plurality of calculation methods each of which has priority in accordance with a type of noise information are set;

detecting, by the cuff, a signal waveform representing a change in an oscillation amplitude and a change in a cuff pressure;

determining the type of the noise information contained in the detected signal waveform;

deciding the blood pressure from at least one candidate value for the blood pressure, which is calculated by one of the calculation methods that has the priority with respect to the determined type of the noise information; and displaying the decided blood pressure.

The calculation methods may calculate the candidate values based on a relationship between the cuff pressure and the oscillation amplitude, respectively and include at least two of a normal calculation method, a moving average calculation method, a calculation method that uses wavelet processing, a calculation method that uses filter bank processing, and a calculation method that uses FFT (fast Fourier transform) processing.

The method may further include calculating the candidate values for the blood pressure by means of at least two of the calculation methods regardless of the type of the noise information.

The method may further include calculating the candidate value for the blood pressure by means of the one of the calculation method that has the highest priority with respect to the determined type of the noise information.

The type of the noise information may include: a noise due to body motion of the living body which includes a single noise, an oscillatory noise, a low-frequency noise; and arrythmia due to disorder.

When the type of the noise information is the single noise, a normal calculation method included in the calculation methods may have priority.

When the type of the noise information is the oscillatory noise, a calculation method that uses wavelet processing, a calculation method that uses filter bank processing, and a calculation method that uses FFT (fast Fourier transform) processing, which are included in the calculation methods, may have this order of priority.

When the type of the noise information is the low-frequency noise, a normal calculation method and a calculation method that uses FFT (fast Fourier transform) processing, which are included in the calculation methods, may have this order of priority.

When the type of the noise information is the arrythmia, a normal calculation method, a moving average calculation method, a calculation method that uses wavelet processing, and a calculation method that uses filter bank processing, which are included in the calculation methods, may have this order of priority.

The method may further include determining whether the noise information is contained in the detected signal waveform. When the noise information is not contained in the detected signal waveform, a normal calculation method included in the calculation methods may have priority.

According to the invention, there is also provided a non-invasive blood pressure measurement apparatus, comprising:

a cuff, being inflatable and deflatable and adapted to be fitted on a part of a living body a memory, adapted to store a plurality of calculation methods each of which has priority in accordance with a type of noise information;

a detector, operable to detect, by the cuff, a signal waveform representing a change in an oscillation amplitude and a change in a cuff pressure;

a determiner, operable to determine the type of the noise information contained in the detected signal waveform; and a decider, operable to decide the blood pressure from at least one candidate value for the blood pressure, which is calculated by one of the calculation methods that has the priority with respect to the determined type of the noise information, to display the blood pressure.

BRIEF DESCRIPTION OF THE DRAWINGS

FIGS. 3A and 3B show examples of noise, which are determined as an oscillatory noise in the blood pressure measurement method of the non-invasive blood pressure measurement apparatus according to the present invention, in which FIG. 3A is an explanatory diagram of the noise example illustrating multiple changes in amplitude values at predetermined intervals, and FIG. 3B is an explanatory diagram of the noise example illustrating irregular changes in amplitude values at predetermined intervals.

FIGS. 4A and 4B show examples of noise, which are determined as a low frequency noise in the blood pressure measurement method of the non-invasive blood pressure measurement apparatus according to the present invention, in which FIG. 4A is an explanatory diagram illustrating an example of noise when the waveform of a cuff pressure having the high-frequency component eliminated therefrom deviates from a target value, and FIG. 4B is an explanatory diagram illustrating an example of noise when an actual pressing/decompressing speed of the cuff pressure deviates from a target speed thereof.

DETAILED DESCRIPTION OF PREFERRED EMBODIMENTS

Hereinafter, an embodiment of a blood pressure calculation method for use in a non-invasive blood pressure measurement apparatus according to the present invention will be described in detail, with reference to the accompanying drawings.

First, a basic configuration of the blood pressure calculation method for use in the non-invasive blood pressure measurement apparatus according to the present invention has the following aspects. The non-invasive blood pressure measurement apparatus is configured such that a cuff being inflatable and deflatable while being fitted on a part of a living body detects a change in an oscillation amplitude generated from arterial pulsation and a change in a cuff pressure, and that a plurality of calculation methods is prepared (stored in the non-invasive blood pressure measurement apparatus) as a calculation method for calculating a blood pressure value based on the relationship between the change in the cuff pressure and the change in the oscillation amplitude so that respective blood pressure values are calculated by the plurality of calculation methods. The blood pressure calculation method includes the steps of: (1) determining a type of a noise due to body motion of the living body or of arrythmia due to disorder, contained in a signal waveform detected by the cuff, representing the change in the oscillation amplitude and the change in the cuff pressure; and (2) assigning a priority order to the respective calculation methods that can calculate an appropriate blood pressure value in accordance with each of the types of the noise or the arrythmia contained in the detection signal waveform, and selecting and displaying, as the optimum blood pressure value, a blood pressure value calculated by a calculation method that has the highest priority order with respect to the detection signal waveform.

In this case, the plurality of calculation methods prepared for calculation of blood pressure values and calculating the blood pressure value based on the relationship between the cuff pressure and the oscillation amplitude includes at least two calculation methods selected from a group consisting of a normal calculation method, a moving average calculation method, a calculation method that uses wavelet processing, a calculation method that uses filter bank processing, and a calculation method that uses FFT (fast Fourier transform) processing.

Embodiment 1

Figure 1:
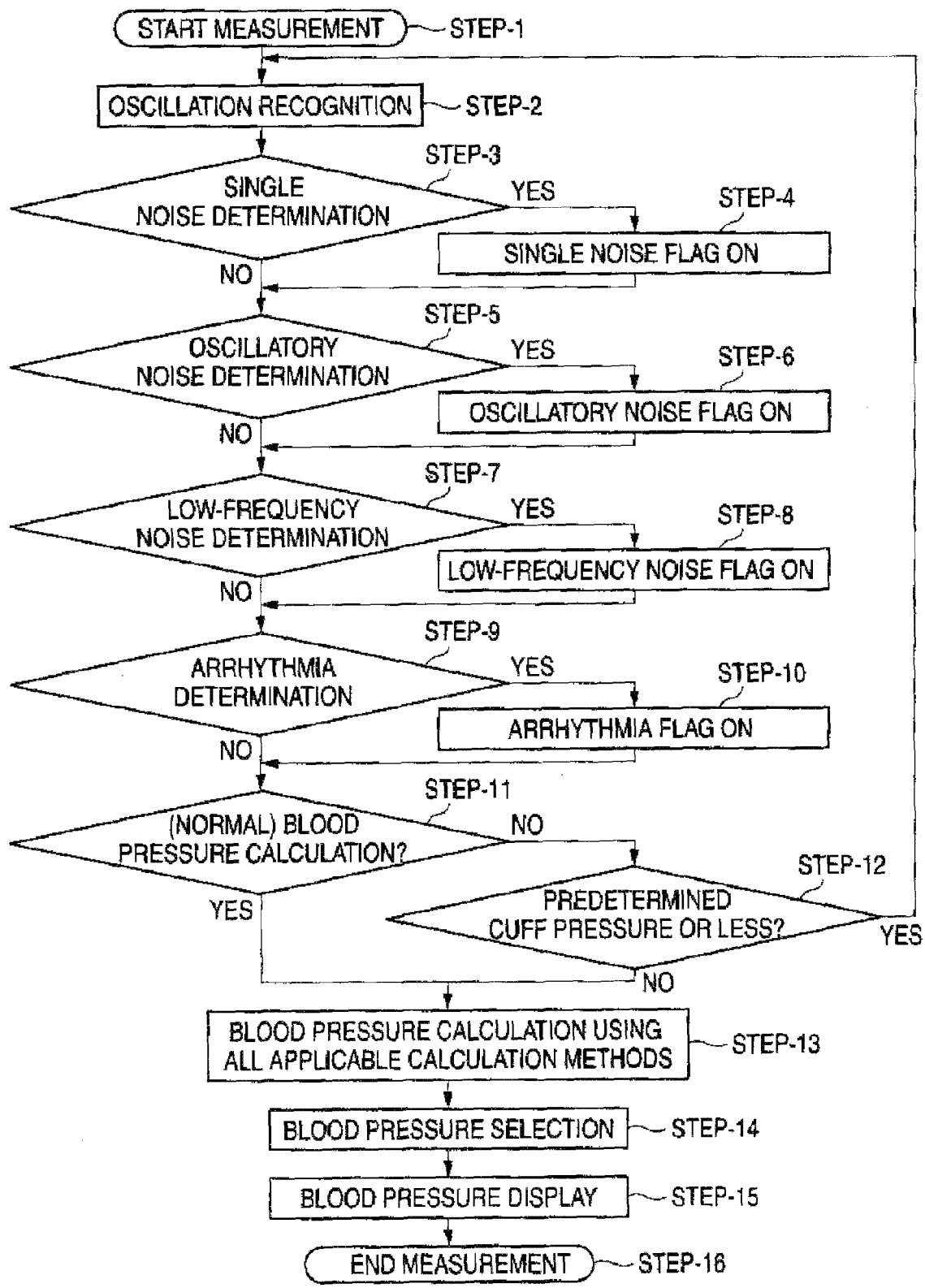
FIG. 1 is a flow chart of a blood pressure calculation program, illustrating an embodiment of a blood pressure calculation method of a non-invasive blood pressure measurement apparatus according to the present invention.

FIG. 1 is a flow chart of a blood pressure calculation program, illustrating an embodiment of a blood pressure calculation method of a non-invasive blood pressure measurement apparatus according to the present invention.

In the embodiment illustrated in FIG. 1, when determining a type of a noise due to body motion of the living body or of arrythmia due to disorder, contained in a signal waveform detected by the cuff, representing the change in the oscillation amplitude and the change in the cuff pressure, the blood pressure value is calculated by means of all calculation methods prepared therein regardless of the type of the noise or the arrythmia contained in the detection signal waveform, thereby selecting and displaying, as the optimum blood pressure value, a blood pressure value calculated by a calculation method that has the highest priority order among the calculation methods corresponding to the determined type of the noise or the arrythmia.

Next, a blood pressure calculation method according to the present embodiment will be described with reference to the flow chart of FIG. 1. A method of determining the type of the noise or the arrythmia due to body motion or disorder of a living body, contained in the signal waveform of the change in the cuff pressure and the change of the oscillation amplitude detected by the cuff will be described later.

First, a cuff being inflatable and deflatable is fitted on a part of a subject's living body, and a measurement is started to detect a change in an oscillation amplitude generated from arterial pulsation and a change in a cuff pressure (STEP 1). Subsequently, a change in the oscillation amplitude is recognized based on the measurement (STEP 2) to perform a determination on a single noise (details of which will be described later) (STEP 3). When the single noise is identified, a single noise flag is turned on in a blood pressure calculation program for calculating a blood pressure value (STEP 4). When the single noise is not identified, or when the single noise flag is turned on, the flow proceeds to a determination on an oscillatory noise (details of which will be described later) (STEP 5).

When the oscillatory noise is identified in the determination on the oscillatory noise (STEP 5), an oscillatory noise flag is turned on in the blood pressure calculation program for calculating the blood pressure value (STEP 6). When the oscillatory noise is not identified, or when the oscillatory noise flag is turned on, the flow proceeds to a determination on a low-frequency noise (details of which will be described later) (STEP 7).

When the low-frequency noise is identified in the determination on the low-frequency noise (STEP 7), a low-frequency noise flag is turned on in the blood pressure calculation program for calculating the blood pressure value (STEP 8). When the low-frequency noise is not identified, or when the low-frequency noise flag is turned one the flow proceeds to a determination on arrythmia (details of which will be described later) (STEP 9).

When the arrythmia is identified in the determination on the arrythmia (STEP 9), an arrythmia flag is turned on in the blood pressure calculation program for calculating the blood pressure value (STEP 10). When the arrythmia is not identified, or when the arrythmia flag is turned on, the flow proceeds to a determination as to whether or not blood pressure calculation can be carried out by means of at least a normal blood pressure calculation method (STEP 11).

When the blood pressure calculation by means of at least the normal blood pressure calculation method is determined as being not suitable based on the change in the oscillation amplitude generated from arterial pulsation and the change in the cuff pressure in the determination as to whether or not the blood pressure calculation can be carried out (STEP 11), it is determined as to whether or not the cuff pressure detected by the cuff has reached a preset value (e.g., 180 mmHg, which can be set in an arbitrary manner) (STEP 12). When the cuff pressure is the preset value or less, the flow returns to the step (STEP 2) of recognizing the change in the oscillation amplitude, which is detected and measured once again, and the above-described steps of performing determination on the various noises and the arrythmia (STEP 3 to STEP 11).

When the blood pressure calculation is determined as being possible in the determination (STEP 11), or when the cuff pressure is determined to have reached the preset value (STEP 12), the blood pressure value is calculated by means of all of a plurality of calculation methods prepared in advance (STEP 13).

Next, the optimum blood pressure value is selected from a plurality of blood pressure values calculated by all the calculation methods (STEP 14). The selection of the optimum blood pressure value includes (1) determination as to whether the calculated blood pressure values are appropriate as a blood pressure value; (2) selection of the calculated blood pressure value calculated by means of an appropriate calculation method corresponding to the type of the noise or the arrythmia which is detected, measured and determined; and (3) comparing the numbers of oscillations used for calculation of the blood pressure values to thereby select the blood pressure value calculated using the largest number of oscillations as the optimum blood pressure value. Details of this will be described later.

Thereafter, the blood pressure value selected as the optimum blood pressure value (STEP 14) is displayed (STEP 15), and the measurement is completed (STEP 16).

Next, the determination on the type of the noise and the arrythmia which is detected and measured will be described in detail. It is to be noted that although in the present embodiment, the single noise, the oscillatory noise, and the low-frequency noise are illustrated as an example of the type of the noise and the arrythmia, the type is not limited to this kind of noise, and the determination may be made on other kind of noise.

Figure 2:
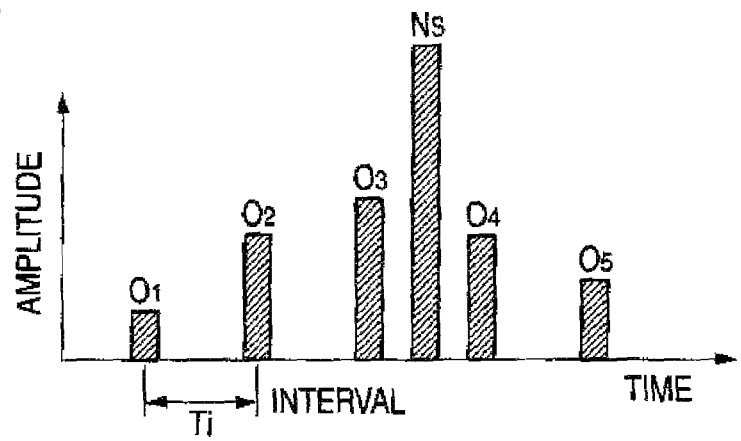
FIG. 2 is an explanatory diagram illustrating examples of noise, which are determined as a single noise in the blood pressure measurement method of the non-invasive blood pressure measurement apparatus according to the present invention.

FIG. 2 illustrates a method of determining the single noise. For example, from the mutual relationship between amplitude intervals Ti of the detected and measured oscillation amplitudes O1 to O5, including amplitude values thereof, an oscillation amplitude Ns outside a predetermined threshold value is identified as the single noise.

Figure 3A:
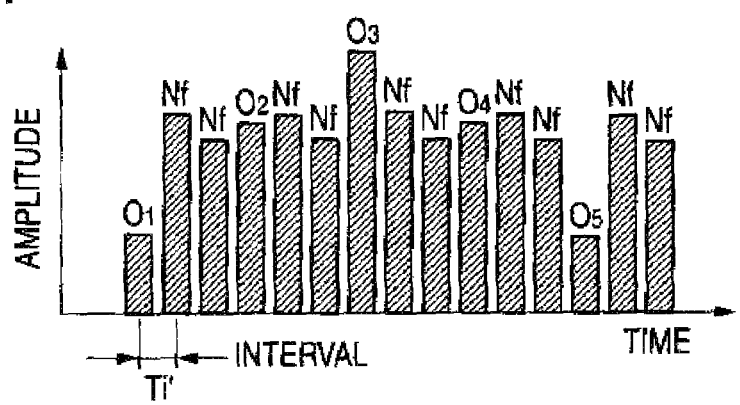
Figure 3B:
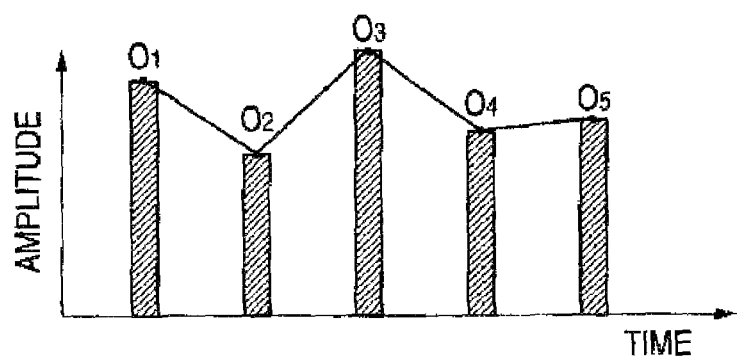

FIGS. 3A and 3B illustrate a method of determining the oscillatory noise. For example, when the number of oscillation amplitude pairs of which the amplitude intervals Ti' (occurrence intervals of adjacent two oscillation amplitudes) of the detected and measured oscillation amplitudes O1 to O5 is smaller than 250 msec, as shown in FIG. 3A, is larger than a predetermined number (e.g., 5), the oscillation amplitude pairs are identified as the oscillatory noise.

Moreover, as shown in FIG. 5B, when the amplitude values of the detected and measured oscillation amplitudes O1 to O5 vary irregularly and when the number of times a slope of a line that connects the amplitude values is changed is larger than a predetermined number (e.g., 5), the oscillation amplitudes are identified as the oscillatory noise.

Figure 4A:
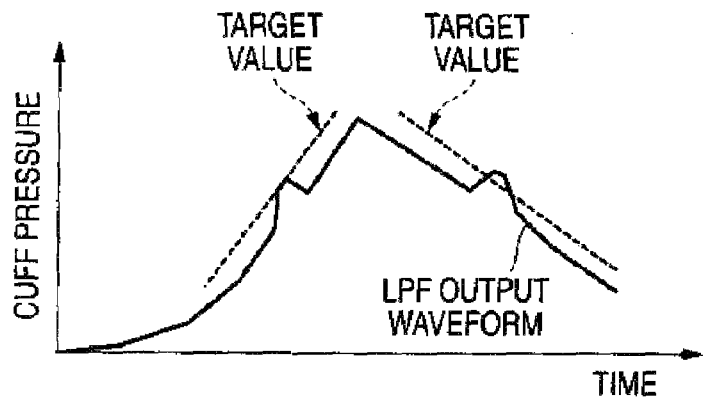
Figure 4B:
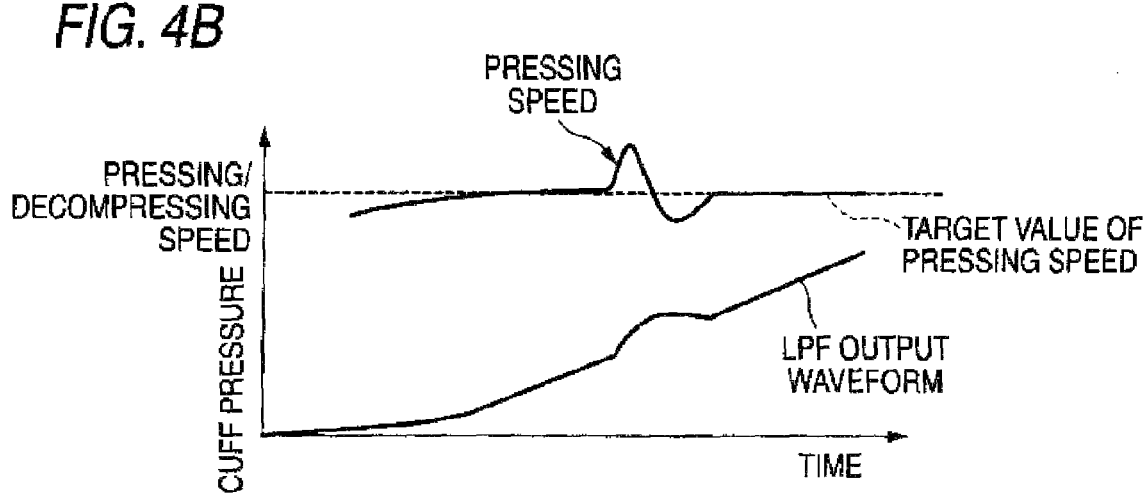

FIGS. 4A and 4B illustrate a method of determining the low-frequency noise. For example, a waveform of the cuff pressure obtained by inflating and deflating a cuff is passed through a low-pass filter (LPF) having an appropriate time constant to eliminate a high-frequency component, whereby a waveform is obtained as shown in FIG. 4A. When a difference between the pressing speed or the decompressing speed (abruptly changing portions of the waveform depicted by a solid line) and a target value thereof (depicted by a broken line) deviates from an arbitrary preset value, it is identified as being the low-frequency noise.

Moreover, as shown in FIG. 4B, when a difference between an actual pressing speed (decompressing speed) of the cuff pressure and a target value thereof (depicted by a broken line) deviates from an arbitrary preset value, it is identified as being the low-frequency noise.

Although not illustrated for the arrythmia, the arrythmia is observed when the heart beats or the amplitude intervals of the oscillation amplitudes are not constant. In this respect, when a deviation of the amplitude intervals of the detected and measured oscillation amplitudes deviates from an arbitrary preset value, it is identified as being the arrythmia.

Figure 5:
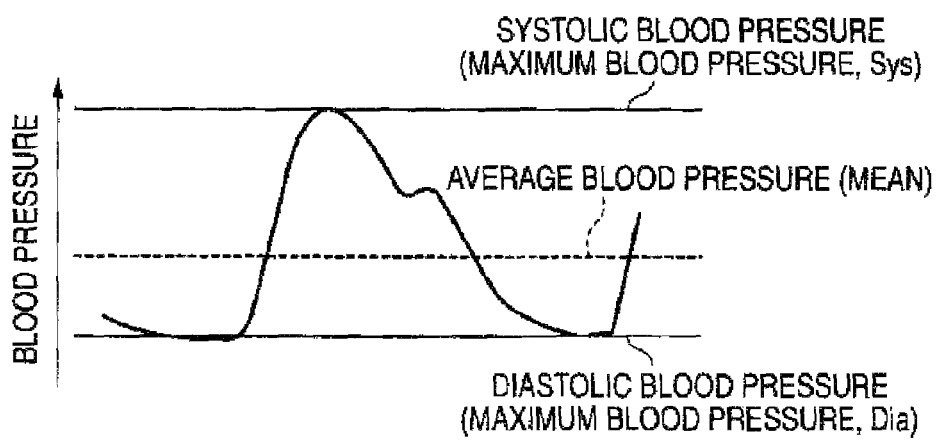
FIG. 5 is an explanatory diagram for explaining the relationship between a systolic blood pressure ("Sys" value), a diastolic blood pressure ("Dia" value), and an average blood pressure ("Mean") in the blood pressure measurement method of the non-invasive blood pressure measurement apparatus according to the present invention.
Figures 6, 7:
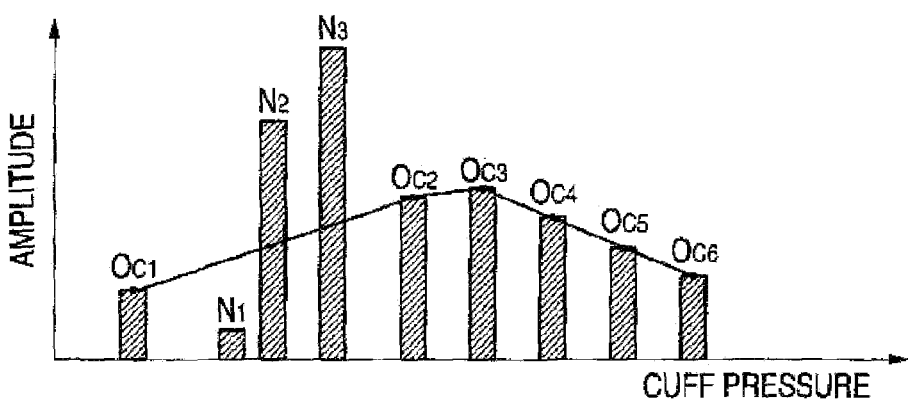
FIG. 6 is an explanatory diagram illustrating a table showing the relationship between a noise determination result and a selected calculation method in the blood pressure measurement method of the non-invasive blood pressure measurement apparatus according to the present invention.
FIG. 7 is an explanatory diagram illustrating a method for selecting the optimum value from the blood pressure value calculated by the respective calculation methods selected as a result of the noise determination in the blood pressure measurement method of the non-invasive blood pressure measurement apparatus according to the present invention.

FIGS. 5 to 7 illustrate specific examples when the selection of the optimum blood pressure value (STEP 14) is performed in the blood pressure calculation program shown in the first embodiment. Hereinafter, this will be described with reference to FIGS. 5 to 7.

FIG. 5 illustrates a method of determining as to whether or not the blood pressure values calculated by means of the above-described calculation methods for calculation of the blood pressure values are appropriate. The calculation methods includes a normal calculation method, a moving average calculation method, a calculation method that uses wavelet processing a calculation method that uses filter bank processing, and a calculation method that uses FFT (fast Fourier transform) processing. In general, as shown in FIG. 5, a systolic value "Sys," which is a systolic (maximum and highest) pressure, a diastolic value "Dia," which is a diastolic (minimum and lowest) pressure, and a mean value "Mean," which is an average pressure, satisfy the following relationship:

(Sys-Mean):(Mean-Dia)≈2:1

Therefore, by using this relationship, it can be determined as to whether or not the calculated blood pressure values are appropriate, and the selection of the calculation methods and the selection of the optimum blood pressure value are validated.

FIG. 6 shows a selection example of the calculation methods, illustrating a table showing the relationship between the type of the noise and the arrythmia, which is detected, measured, and determined, and the selected calculation methods. In the first embodiment, among the blood pressure values calculated by means of all the calculation methods, a blood pressure value calculated by the calculation method, which is determined to be appropriate from the relationship illustrated in FIG. 5 and satisfy the relationship illustrated in FIG. 6 is selected. In this case, in the table shown in FIG. 6, the calculation methods corresponding to the determined type of the noise and the arrythmia are configured such that the calculation methods (filled with a circle) are sequentially selected, starting from the leftmost one.

FIG. 7 illustrates a method of selecting the optimum blood pressure value from the blood pressure values calculated by the selected calculation method. In this case, the respective numbers of oscillations used in the respective calculation methods are compared, and the blood pressure value calculated using the largest number of oscillations is selected as the optimum blood pressure value. For example, as illustrated in FIG. 7, the number of oscillations required for the blood pressure calculation in the normal calculation method is six. The number of oscillations in other calculation methods is defined such that the moving average method requires five oscillations, the calculation method that uses the wavelet processing requires five oscillations, the calculation method that uses the filter bank processing requires five oscillations, and the calculation method that uses the fast Fourier transform (FFT) processing requires five oscillations. Therefore, the blood pressure value calculated by the normal calculation method having the largest number of oscillations can be selected as the optimum blood pressure value. When there is a plurality of calculation methods having the largest number of oscillations, the blood pressure value calculated by the calculation method that does not use mathematics is preferentially selected as the optimum blood pressure value. In FIG. 7, N1, N2, and N3 represent noise contained in the oscillation amplitudes, and Oc1 to Oc6 represent oscillation amplitudes used in the blood pressure calculation.

Embodiment 2

Figure 8:
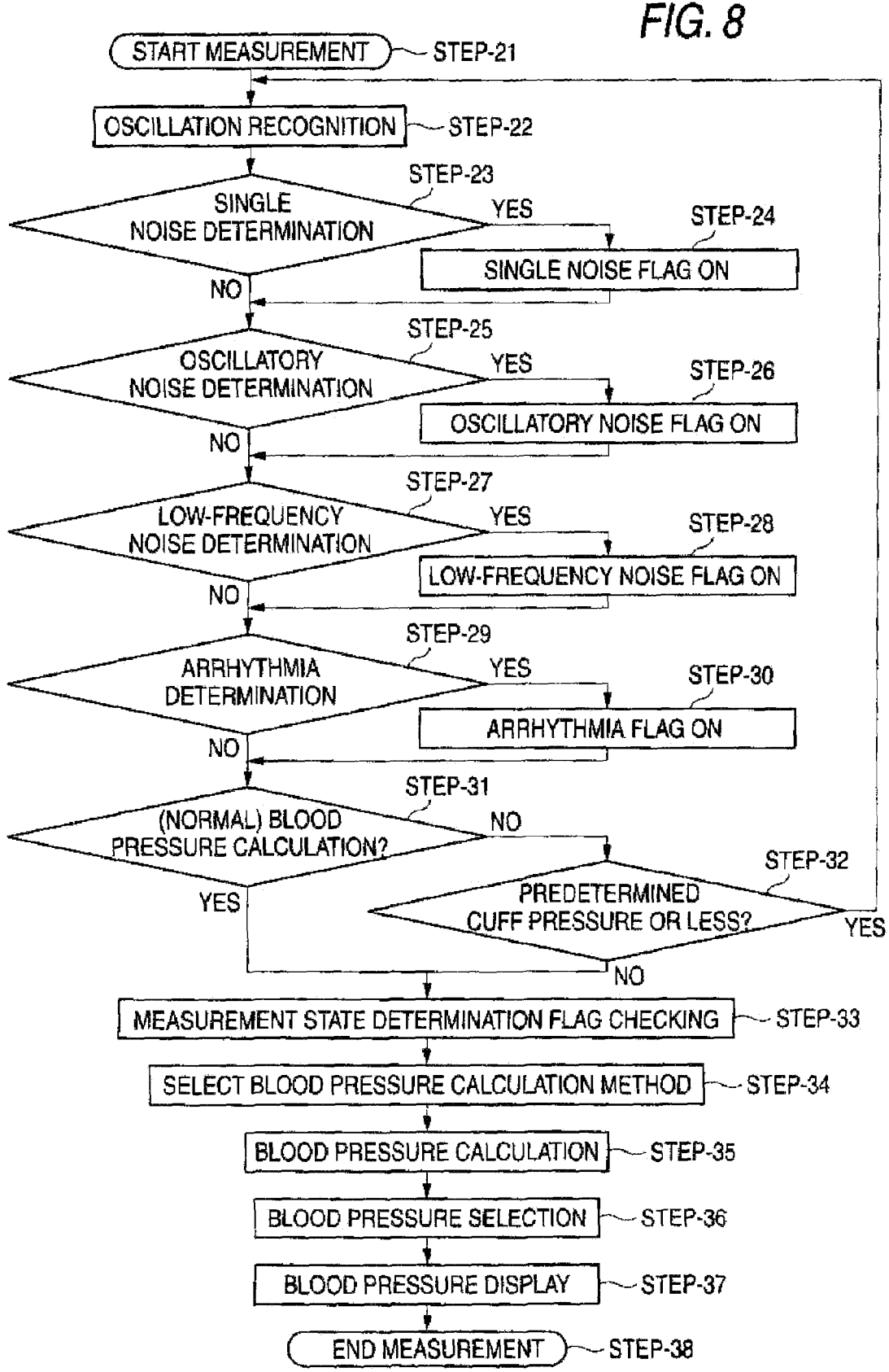
FIG. 8 is a flow chart of a blood pressure calculation program, illustrating another embodiment of a blood pressure calculation method of a non-invasive blood pressure measurement apparatus according to the present invention.

FIG. 8 is a flow chart of a blood pressure calculation program, illustrating another embodiment of a blood pressure calculation method of a non-invasive blood pressure measurement apparatus according to the present invention.

In the embodiment illustrated in FIG. 8, when determining a type of a noise due to body motion of the living body or of arrythmia due to disorder, contained in a signal waveform detected by the cuff, representing the change in the oscillation amplitude and the change in the cuff pressure, the blood pressure value calculated by means of a calculation method prepared to correspond to the type of the noise or the arrythmia contained in the detection signal waveform is selected and displayed as the optimum blood pressure value.

Next, a blood pressure calculation method according to the present embodiment will be described with reference to the flow chart of FIG. 8. A method of determining the type of the noise or the arrythmia due to body motion or disorder of a living body, contained in the signal waveform of the change in the cuff pressure and the change of the oscillation amplitude detected by the cuff is the same as that described above and thus will not be described.

First, a cuff being inflatable and deflatable is fitted on apart of a subject's living body, and a measurement is started to detect a change in an oscillation amplitude generated from arterial pulsation and a change in a cuff pressure (STEP 21). Subsequently, a change in the oscillation amplitude is recognized based on the measurement (STEP 22) to perform a determination on a single noise (STEP 23). When the single noise is identified, a single noise flag is turned on in a blood pressure calculation program for calculating a blood pressure value (STEP 24). When the single noise is not identified, or when the single noise flag is turned on, the flow proceeds to a determination on an oscillatory noise (STEP 25).

When the oscillatory noise is identified in the determination on the oscillatory noise (STEP 25), an oscillatory noise flag is turned on in the blood pressure calculation program for calculating the blood pressure value (STEP 26). When the oscillatory noise is not identified, or when the oscillatory noise flag is turned on, the flow proceeds to a determination on a low-frequency noise (STEP 27).

When the low-frequency noise is identified in the determination on the low-frequency noise (STEP 27), a low-frequency noise flag is turned on in the blood pressure calculation program for calculating the blood pressure value (STEP 28). When the low-frequency noise is not identified, or when the low-frequency noise flag is turned on, the flow proceeds to a determination on arrythmia (STEP 29).

When the arrythmia is identified in the determination on the arrythmia (STEP 29), an arrythmia flag is turned on in the blood pressure calculation program for calculating the blood pressure value (STEP 30). When the arrythmia is not identified, or when the arrythmia flag is turned on, the flow proceeds to a determination as to whether or not blood pressure calculation can be carried out by means of at least a normal blood pressure calculation method (STEP 31).

When the blood pressure calculation by means of at least the normal blood pressure calculation method is determined as being not suitable based on the change in the oscillation amplitude generated from arterial pulsation and the change in the cuff pressure in the determination as to whether or not the blood pressure calculation can be carried out (STEP 31), it is determined as to whether or not the cuff pressure detected by the cuff has reached a preset value (e.g., 180 mmHg, which can be set in an arbitrary manner) (STEP 32). When the cuff pressure is the preset value or less, the flow returns to the step (STEP 22) of recognizing the change in the oscillation amplitude, which is detected and measured once again, and the above-described steps of performing determination on the various noises and the arrythmia (STEP 23 to STEP 31). The contents of the blood pressure calculation program in the blood pressure calculation method according to the second embodiment are the same as the contents of the first embodiment.

When the blood pressure calculation is determined as being possible in the determination (STEP 31), or when the cuff pressure is determined to have reached the preset value (STEP 32), the flags of the noise or the arrythmia which were determined in the steps (STEP 23 to STEP 30) of performing determinations on the various noises and the arrythmia and recorded in the blood pressure calculation program are checked (STEP 33).

When the type of the noise or the arrythmia is determined in the turning on (STEP 33) of the flags of the noise or the arrythmia, corresponding ones of the predetermined calculation methods capable of calculating an appropriate blood pressure value are selected (STEP 34), whereby the blood pressure values are calculated (STEP 35). In this case, a single or a plurality of calculation methods capable of calculating an appropriate blood pressure value, corresponding to the types of the noise or the arrythmia is selected based on the table illustrated in FIG. 6 and executed.

Next, the optimum blood pressure value is selected from a plurality of blood pressure values calculated by all the calculation methods (STEP 36). The selection of the optimum blood pressure value includes (1) determination as to whether the calculated blood pressure values are appropriate as a blood pressure value (see FIG. 5); and (2) comparing the numbers of oscillations used for calculation of the blood pressure values to thereby select the blood pressure value calculated using the largest number of oscillations as the optimum blood pressure value (see FIG. 7).

Thereafter, the blood pressure value selected as the optimum blood pressure value (STEP 3C) is displayed (STEP 37), and the measurement is completed (STEP 38).

Embodiment 3

By using the blood pressure calculation method of the non-invasive blood pressure measurement apparatus described above with reference to FIGS. 1 to 8, it is possible to configure a blood pressure calculation apparatus capable of calculating and displaying the correct blood pressure and to manufacture a non-invasive blood pressure measurement apparatus having the blood pressure calculation apparatus. In such a case, it is possible to determine a type of a noise due to subject's body motion or arrythmia due to disorder from a change in a cuff pressure or a change in an oscillation amplitude detected or measured from a subject and to calculate and display the optimum blood pressure of the subject in a quick and appropriate manner by means of a blood pressure calculation method that can best cope with the determined type of the noise or the arrythmia. Therefore, it is possible to provide a non-invasive blood pressure measurement apparatus which can increase accuracy of blood pressure measurement, ensure emergency usability, and greatly increase general versatility.

Hereinabove, suitable embodiments of the present invention have been described but the present invention is not limited to these embodiments. For example, when determining the type of the detected and measured noise due to subject's body motion or the arrythmia due to disorder, various changes can be made in the kind of or the determination sequence of the type. Moreover, other additional known calculation methods may be used for the blood pressure calculation method. Therefore, it should be noted that numerous changes in the details of construction and arrangement of parts may be made without departing from the spirit of the present invention.

What is claimed is:

1. A method of calculating a blood pressure using a memory to store a plurality of calculation methods, comprising:

providing a non-invasive blood pressure measurement apparatus which includes a cuff, a determiner, a decider and the memory, the cuff being inflatable and deflatable and adapted to be fitted on a part of a living body and in which a plurality of calculation methods each of which has priority in accordance with a type of noise information are set;

detecting, by a detector included in the cuff, a signal waveform representing a change in an oscillation amplitude and a change in a cuff pressure;

determining through the determiner the type of the noise information contained in the detected signal waveform;

determining through the determiner a priority status from highest priority to lowest priority for each of the calculation methods based on the determining of the type of the noise information contained in the detected signal waveform;

deciding through the decider the blood pressure from at least one candidate value for the blood pressure, which is calculated by one of the calculation methods stored on the memory that has the highest priority status with respect to the determined type of the noise information; and displaying the decided blood pressure.

2. The method according to claim 1, wherein the calculation methods calculate the candidate values based on a relationship between the cuff pressure and the oscillation amplitude, respectively and include at least two of a first calculation method, a moving average calculation method, a calculation method that uses wavelet processing, a calculation method that uses filter bank processing, and a calculation method that uses FFT (fast Fourier transform) processing, wherein the first calculation method is different from each of the moving average calculation method, the calculation method that uses wavelet processing, the calculation method that uses filter bank processing, and the calculation method that uses FFT processing.

3. The method according to claim 1, further comprising: calculating the candidate values for the blood pressure by means of at least two of the calculation methods regardless of the type of the noise information.

4. The method according to claim 1 further comprising: calculating the candidate value for the blood pressure by means of the one of the calculation method that has the highest priority with respect to the determined type of the noise information.

5. The method according to claim 1, wherein the type of the noise information includes:

a noise due to body motion of the living body which includes a single noise, an oscillatory noise, a low-frequency noise; and arrhythmia due to disorder.

6. The method according to claim 5, wherein when the type of the noise information is the single noise, a first calculation method included in the calculation methods has the highest priority.

7. The method according to claim 5, wherein when the type of the noise information is the oscillatory noise, a calculation method that uses wavelet processing, a calculation method that uses filter bank processing, and a calculation method that uses FFT (fast Fourier transform) processing, which are included in the calculation methods, have this order of priority.

8. The method according to claim 5, wherein when the type of the noise information is the low-frequency noise, a first calculation method and a calculation method that uses FFT (fast Fourier transform) processing, which are included in the calculation methods, have this order of priority.

9. The method according to claim 5, wherein when the type of the noise information is the arrhythmia, a first calculation method, a moving average calculation method, a calculation method that uses wavelet processing, and a calculation method that uses filter bank processing, which are included in the calculation methods, have this order of priority.

10. The method according to claim 1, further comprising: determining whether the noise information is contained in the detected signal waveform, wherein when the noise information is not contained in the detected signal waveform, a first calculation method included in the calculation methods has the highest priority.

* * * * *